(12) United States Patent
Rodriguez-Sarmiento et al.

(10) Patent No.: US 7,456,210 B2
(45) Date of Patent: Nov. 25, 2008

(54) BENZYLOXY DERIVATIVES

(75) Inventors: Rosa Maria Rodriguez-Sarmiento, Basel (CH); Wolfgang Wostl, Grenzach-Wyhlen (DE); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 539 days.

(21) Appl. No.: 11/190,626

(22) Filed: Jul. 27, 2005

(65) Prior Publication Data
US 2006/0025599 A1 Feb. 2, 2006

(30) Foreign Application Priority Data
Aug. 2, 2004 (EP) .................. 04103710

(51) Int. Cl.
*A61K 31/4015* (2006.01)
*C07D 207/12* (2006.01)

(52) U.S. Cl. ............... 514/424; 548/131; 548/203; 548/311.1; 548/541; 548/551; 514/364; 514/397; 514/408; 514/422

(58) Field of Classification Search .......... 548/131, 548/146, 202, 203, 300.1, 311.1, 314.7, 541, 548/543, 551; 514/364, 365, 397, 408, 422, 514/424
See application file for complete search history.

(56) References Cited

U.S. PATENT DOCUMENTS

| 7,037,935 | B2 * | 5/2006 | Iding et al. | 514/423 |
| 7,122,562 | B2 * | 10/2006 | Iding et al. | 514/343 |
| 7,151,111 | B2 * | 12/2006 | Iding et al. | 514/343 |
| 7,235,581 | B2 * | 6/2007 | Jolidon et al. | 514/424 |

FOREIGN PATENT DOCUMENTS

| WO | WO 96/40095 | 12/1996 |
| WO | WO 97/33572 | 9/1997 |
| WO | WO 01/34172 | 5/2001 |
| WO | WO 2004/026826 A1 | 4/2004 |
| WO | WO 2004/026827 | 4/2004 |

OTHER PUBLICATIONS

Jolidon et al (2004): STN International HCAPLUS database, (Columbus, Ohio), Accession No.: 2004:267295.*
Database Registry, XP002363144 (2002).
Database Registry, XP002363145 (2002).
Database Registry, XP002363146 (2002).
Database Registry, XP002363147 (2002).
Bach et al., Proc. Natl. Acad. Sci. vol. 85: pp. 4934-4938 (1988).
Cesura & Pletscher, Prog. Drug Research vol. 38: pp. 171-297 (1992).
Fowler et al., J. Neural. Transm. vol. 49: pp. 1-20 (1980).
Benedetti et al., Biochem. Pharmacol. vol. 38: pp. 555-561 (1989).
Saura et al., Neuroscience vol. 70: pp. 755-774 (1996).
Bentué-Ferrer et al., CNS Drugs vol. 6: pp. 217-236 (1996).
Gardner et al. J. Clin. Psychiatry vol. 57: pp. 99-104 (1996).
Schlaeger & Christensen, Cytotechnology vol. 30: pp. 71-83 (1999).
Zhou & Panchuk-Voloshina, Analytical Biochemistry vol. 253: pp. 169-174 (1997).

* cited by examiner

*Primary Examiner*—Golam M Shameem
(74) *Attorney, Agent, or Firm*—George W. Johnston; Patricia S. Rocha-Tramaloni; Kimberly J. Prior

(57) ABSTRACT

The present invention relates to compounds of formula I

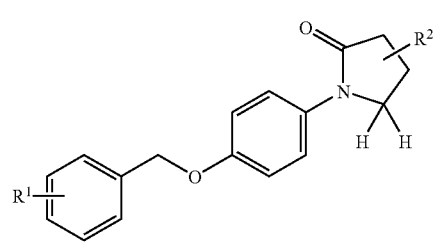

wherein $R^1$ and $R^2$ are as defined in the specification and to pharmaceutically acceptable salts thereof for the treatment of diseases, which are mediated by monoamine oxidase B inhibitors, for example Alzheimer's disease and senile dementia.

16 Claims, No Drawings

BENZYLOXY DERIVATIVES

BACKGROUND OF THE INVENTION

Monoamine oxidase (MAO) is a flavin-containing enzyme responsible for the oxidative deamination of endogenous monoamine neurotransmitters such as dopamine, serotonin, adrenaline, or noradrenaline, and trace amines, e.g. phenyl-ethyl-amine; as well as a number of amine xenobiotics. The enzyme exists in two forms, MAO-A and MAO-B, encoded by different genes (A. W. Bach et al., *Proc. Natl. Acad. Sci. USA* 1988, 85, 4934-4938) and differing in tissue distribution, structure and substrate specificity. MAO-A has higher affinity for serotonin, octopamine, adrenaline, and noradrenaline; whereas the natural substrates for MAO-B are phenyl-ethylamine and tyramine. Dopamine is thought to be oxidised by both isoforms. MAO-B is widely distributed in several organs including brain (A. M. Cesura and A. Pletscher, Prog. Drug Research 1992, 38, 171-297). Brain MAO-B activity appears to increase with age. This increase has been attributed to the gliosis associated with aging (C. J. Fowler et al., *J. Neural. Transm.* 1980, 49, 1-20). Additionally, MAO-B activity is significantly higher in the brains of patients with Alzheimer's disease (P. Dostert et al., *Biochem. Pharmacol.* 1989, 38, 555-561) and it has been found to be highly expressed in astrocytes around senile plaques (Saura et al., *Neuroscience* 1994, 70, 755-774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in *CNS Drugs* 1996, 6, 217-236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99-104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The present invention provides benzyloxy derivatives of formula I

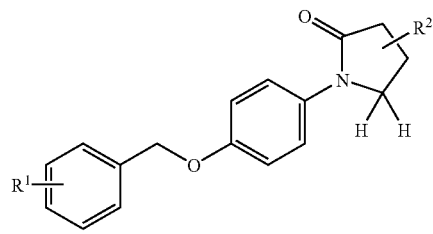

wherein
$R^1$ is halogen;
$R^2$ is —C(O)NH$_2$, —C(NH$_2$)=N—OH, —C(O)CH$_2$Br, —C(O)N(CH$_3$)OCH$_3$, CN or —C(O)-lower alkyl, or is a 5-membered heteroaryl group containing 2 or 3 heteroatoms selected from the group consisting of N, O and S, optionally substituted by $R^3$, wherein $R^3$ is lower alkyl, —NR'R" or —C(O)R;
R is NR'R", lower alkyl, or lower alkoxy; and
R' and R" are each independently hydrogen or lower alkyl;

and their pharmaceutically acceptable salts thereof.

The invention also provides individual isomers of the compounds of formula I as well as racemic and non-racemic mixtures thereof. The invention further provides methods for preparing such compounds.

Compounds of formula I and their pharmaceutically acceptable salts, as individual isomers of the compounds of formula I as well as racemic and non-racemic mixtures thereof (hereinafter: Pharmaceutical Compound) have pharmacological activity and are useful as pharmaceuticals. In particular, Pharmaceutical Compounds inhibit the activity of monoamine oxidase B.

Pharmaceutical Compounds are accordingly useful as selective inhibitors of monoamine oxidase B, e.g. in the treatment or prevention of diseases and conditions in which activity of monoamine oxidase B plays a role or is implicated. Such conditions include in particular acute and/or chronic neurological disorders.

Acute and/or chronic neurological disorders include psychosis, schizophrenia, Alzheimer's disease, cognitive disorders and memory deficits like mild cognitive impairment, age-related cognitive decline, vascular dementia, Parkinsons's disease, memory impairment associated with depression or anxiety, Down's syndrome, stroke, traumatic brain injury, and attention deficit disorder. Other treatable indications are restricted brain function caused by bypass operations or transplants, poor blood supply to the brain, spinal cord injuries, head injuries, hypoxia caused by pregnancy, cardiac arrest and hypoglycemia. Further treatable indications are acute and chronic pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychotic episodes, opiate addiction, anxiety, vomiting, dyskinesia and depression.

Thus, the present invention provides pharmaceutical compositions which comprise a therapeutically effective amount of a compound of the invention and a pharmaceutically acceptable carrier. The invention further provides a method for treating diseases and conditions in which are mediated by monoamine oxidase B activity.

In one embodiment, the invention provides a method for the treatment of Alzheimer's disease. In another embodiment, the invention provides a method for the treatment of mild cognitive impairment or senile dementia.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "lower alkyl" used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine.

"Lower alkoxy" means the residue —O—R, wherein R is a lower alkyl residue as defined herein. Examples of alkoxy radicals include, but are not limited to, methoxy, ethoxy, isopropoxy, and the like.

The term "5-membered heteroaryl, containing 2 or 3 heteroatoms, selected from the group consisting of N, O or S" means a heteroaromatic ring system, selected from the group consisting of [1.2.4]oxadiazolyl, 1,3-thiazolyl, imidazolyl, pyrazolyl, and isoxazolyl. Preferred groups are [1.2.4]oxadiazolyl, 1,3-thiazolyl and imidazolyl.

"Pharmaceutically acceptable" such as pharmaceutically acceptable carrier, excipient, salts, etc., means pharmacologically acceptable, generally safe, substantially non-toxic to the subject to which the particular compound is administered, and neither biologically nor otherwise undesirable.

"Pharmaceutically acceptable salts" of a compound means salts with inorganic or organic acids or bases that possess the desired pharmacological activity of the parent compound. These salts are derived from an inorganic or organic acid or base.

Such salts include:
(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, 2,2,2-trifluoroacetic acid, and the like; or
(2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

Furthermore, as used herein, a "mammal in need of treatment of an acute and/or chronic neurological disorder" means a mammal, e.g. a human, that is suffering from, or is at risk of suffering from, an acute and/or chronic neurological disorder.

As used herein, the terms "treat," "treating," "treatment," and the like, as applied to an acute and/or chronic neurological disorder, refer to methods that slow, ameliorate, reduce or reverse such a disorder or any symptoms associated with said disorder, as currently afflicting the subject.

The present invention provides benzyloxy derivatives of formula I

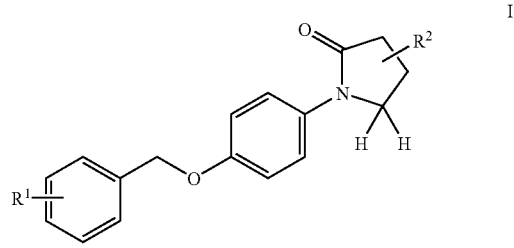

wherein
$R^1$ is halogen;
$R^2$ is —C(O)$NH_2$, —C($NH_2$)=N—OH, —C(O)$CH_2$Br, —C(O)N($CH_3$)$OCH_3$, CN or —C(O)-lower alkyl, or is a 5-membered heteroaryl group containing 2 or 3 heteroatoms selected from the group consisting of N, O and S, optionally substituted by $R^3$, wherein $R^3$ is lower alkyl, —NR'R" or —C(O)R;
R is NR'R", lower alkyl, or lower alkoxy; and
R' and R" are each independently hydrogen or lower alkyl;

or to a pharmaceutically acceptable salt, isomer, racemate, or mixture thereof.

Among compounds of the present invention certain compounds of formula I or pharmaceutically acceptable salts thereof, are preferred. Preferred compounds of formula I comprise those in which $R^2$ is a 5-membered heteroaryl group, containing 2 or 3 heteroatoms, selected from the group consisting of N, O or S, optionally substituted by lower alkyl, —NR'R" or —C(O)R. Such compounds include those of formula IA

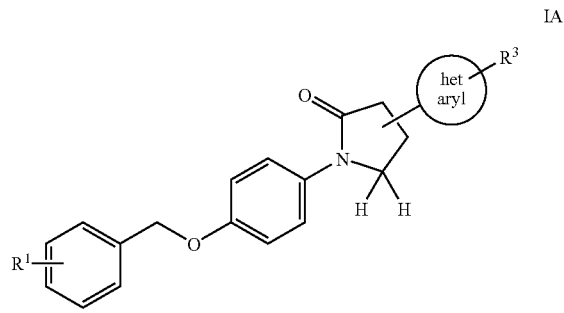

wherein
$R^1$ is halogen;
hetaryl is a 5-membered heteroaryl group containing 2 or 3 heteroatoms selected from the group consisting of [1.2.4]oxadiazolyl, 1,3-thiazolyl, imidazolyl, pyrazolyl, and isoxazolyl;
$R^3$ is lower alkyl, —NR'R" or —C(O)R;
R is NR'R", lower alkyl, or lower alkoxy; and
R' and R" are each independently hydrogen or lower alkyl;

or to a pharmaceutically acceptable salt, isomer, racemate, or mixture thereof.

Compounds of formula IA are, for example, the following:

(R)-1-[4-(3-fluoro-benzyloxy)-phenyl]-4-(5-methyl-[1,2,4]oxadiazol-3-yl)-pyrrolidin-2-one, 3-{(R)-1-[4-(3-fluoro-benzyloxy)-phenyl]-5-oxo-pyrrolidin-3-yl}-[1,2,4]oxadiazole-5-carboxylic acid ethyl ester, 3-{(R)-1-[4-(3-fluoro-benzyloxy)-phenyl]-5-oxo-pyrrolidin-3-yl}-[1,2,4] oxadiazole-5-carboxylic acid amide, (R)-1-[4-(3-fluoro-benzyloxy)-phenyl]-4-(2-methyl-thiazol-4-yl)-pyrrolidin-2-one and (R)-1-[4-(3-fluoro-benzyloxy)-phenyl]-4-(1H-imidazol-4-yl)-pyrrolidin-2-one.

Further compounds of formula I are those, in which $R^2$ is —C(O)NH$_2$, —C(NH$_2$)=N—OH, —C(O)CH$_2$Br, —C(O)N(CH$_3$)OCH$_3$ or —C(O)-lower alkyl, for example (R)-1-[4-(3-fluoro-benzyloxy)-phenyl]-5-oxo-pyrrolidine-3-carboxylic acid amide, (R)-1-[4-(3-fluoro-benzyloxy)-phenyl]-N-hydroxy-5-oxo-pyrrolidine-3-carboxamidine, (R)-1-[4-(3-fluoro-benzyloxy)-phenyl]-5-oxo-pyrrolidine-3-carboxylic acid methoxy-methyl-amide and (R)-4-acetyl-1-[4-(3-fluoro-benzyloxy)-phenyl]-pyrrolidin-2-one.

The compounds of formula I and their pharmaceutically acceptable salts can be manufactured by methods known in the art, for example by processes described below, which processes comprise a) reacting a compound of formula

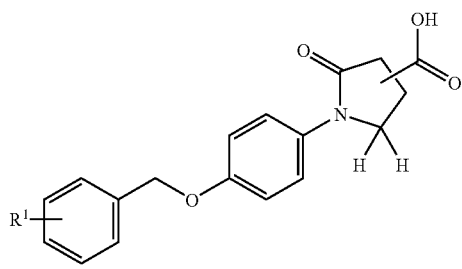

with ammonium acetate in the presence of a condensation reagent like e.g. CDI (1,1'-carbonyl-diimidazole) to produce a compound of formula

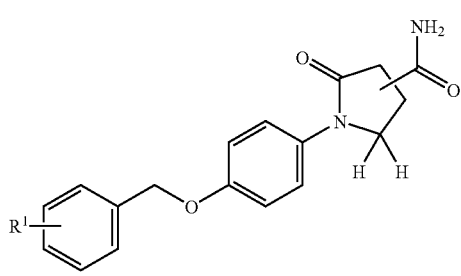

wherein the $R^1$ is as described above, or b) reacting a compound of formula

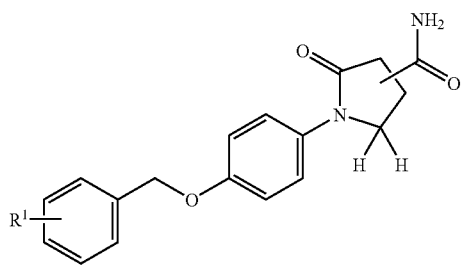

with thionyl chloride to produce a compound of formula

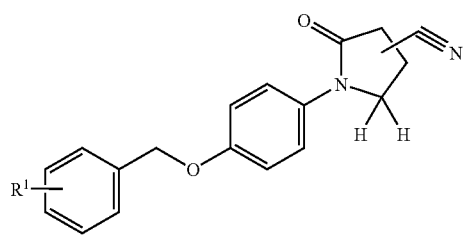

wherein the $R^1$ is as described above, or c) reacting a compound of formula

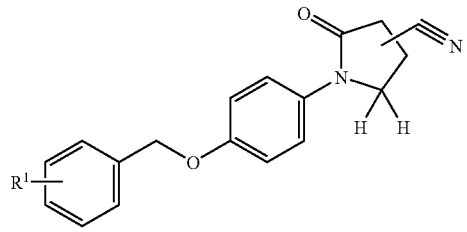

with hydroxylamine to produce a compound of formula

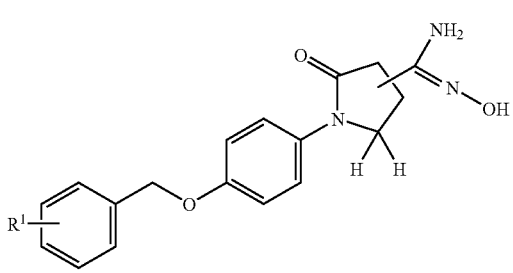

wherein the $R^1$ is as described above, or d) reacting a compound of formula

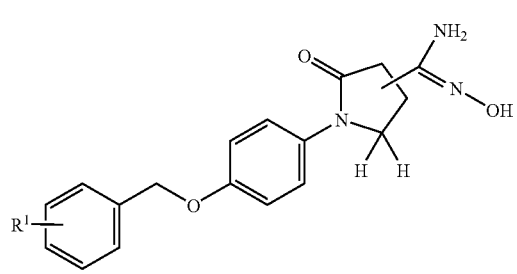
I-2 with acetyl chloride in the presence of a base to produce a compound of formula

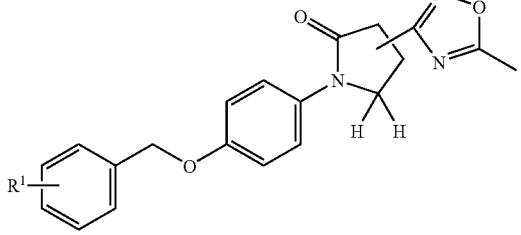
I-3 wherein the R¹ is as described above, or e) reacting a compound of formula

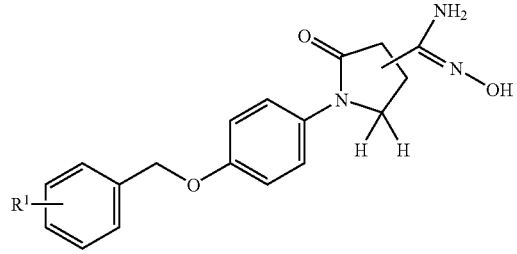
I-2 with ethyl oxalyl chloride to produce a compound of formula

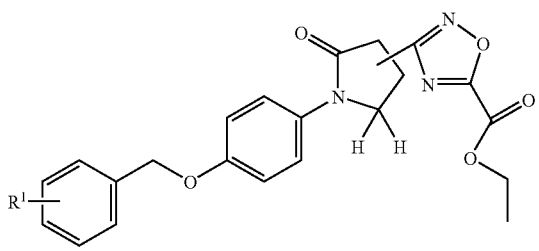
I-4 wherein the R¹ is as described above, or f) reacting a compound of formula

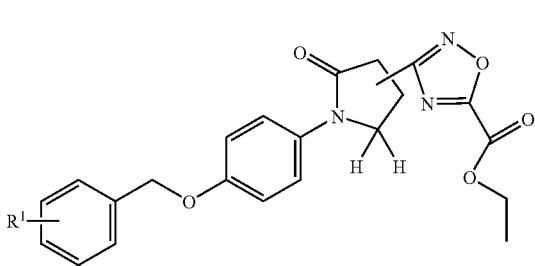
I-4 with NH₄OH to produce a compound of formula

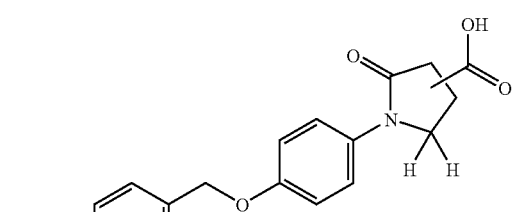
I-5 wherein the R¹ is as described above, or g) reacting a compound of formula

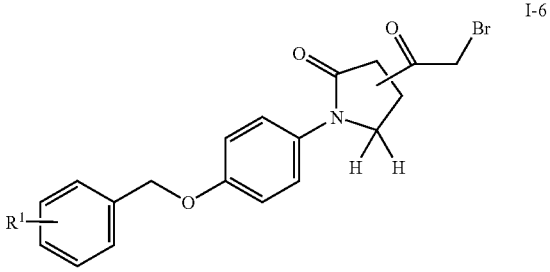
II with thionyl chloride in the presence of N,N'-dimethylformamide and trimethylsilyldiazomethane and HBr to a produce compound of formula

I-6 wherein the R¹ is as described above, or h) reacting a compound of formula

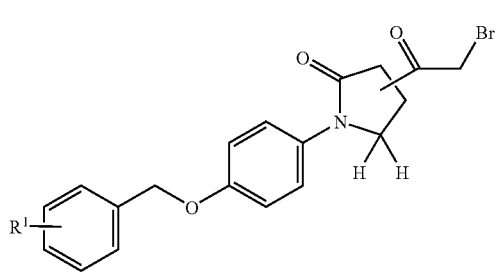

with formamide to produce a compound of formula

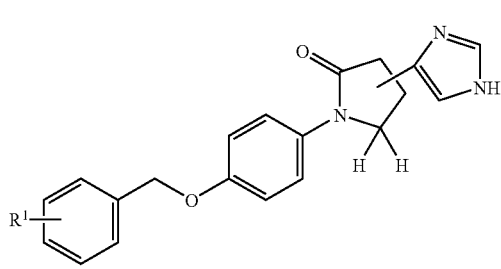

wherein the R¹ is as described above, or
i) reacting a compound of formula

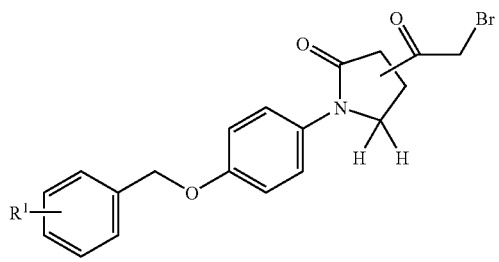

with thioacetamide in THF to produce a compound of formula

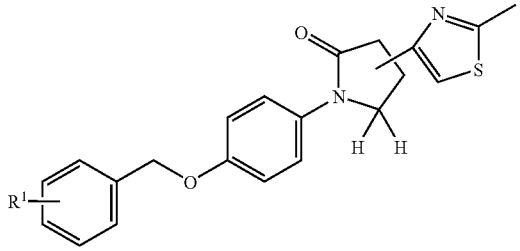

wherein the R¹ is as described above, or j) reacting a compound of formula

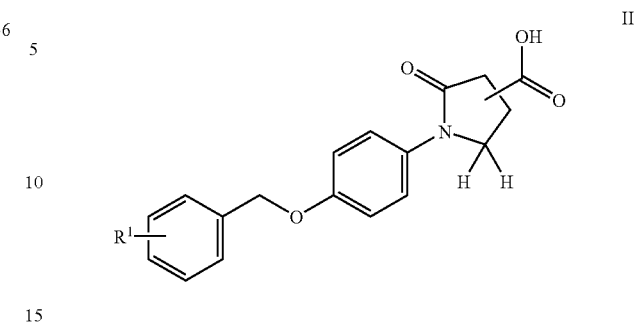

with N,O-dimethylhydroxylamine hydrochloride and CDI to produce a compound of formula

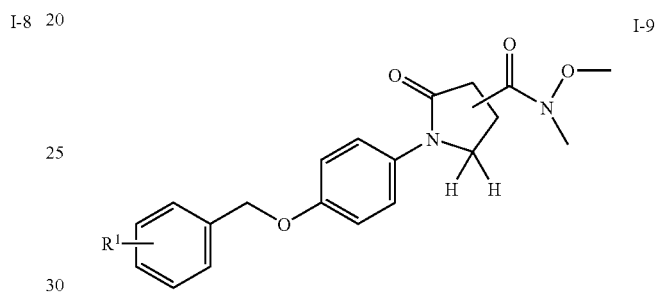

wherein the R¹ is as described above, or
k) reacting a compound of formula

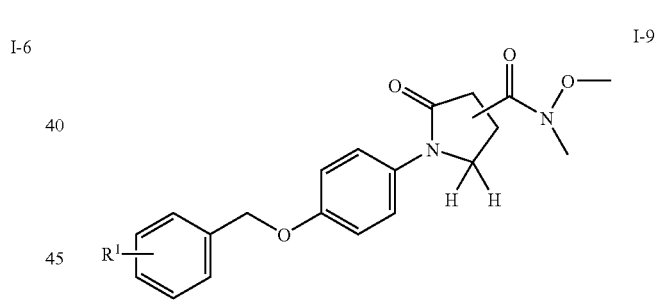

with MeMgBr in THF to produce a compound of formula

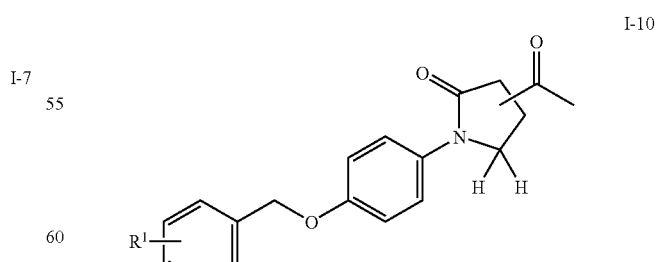

wherein the R¹ is as described above, and, if desired, converting a compound of formula I obtained into pharmaceutically active acid addition salts.

In accordance with the present invention, compounds of formula I can be prepared as shown in schemes 1 and 2. Starting compounds of formula II are known or may be prepared by processes well known in the art. Compounds of formula III are final products encompassed by formula I or may be used as intermediates for the preparation of further compounds of formula I.

Compounds of formula I can be manufactured by reacting a compound of formula II with 1,1'-carbonyl-diimidazole (CDI) in N,N'-dimethylformamide (DMF), followed by the addition of ammonium acetate (scheme 1) to give the corresponding amide of formula I-1. The nitrile compound of formula III can be prepared from the amide by dehydration with a reagent like thionyl chloride preferably at 90° C. Reaction of the compound of formula III with hydroxylamine hydrochloride in the presence of a base, like N,N-diisopropylethylamine, gives the necessary N-hydroxy-carboxamidine of formula I-2, which reacts with acetyl chloride in the presence of a base, like pyridine, to give a compound of formula I-4 or with ethyl oxalyl chloride to give a compound of formula I-3. The corresponding amide of formula I-5 can be prepared from the ester by heating with ammonia in a solvent like methanol.

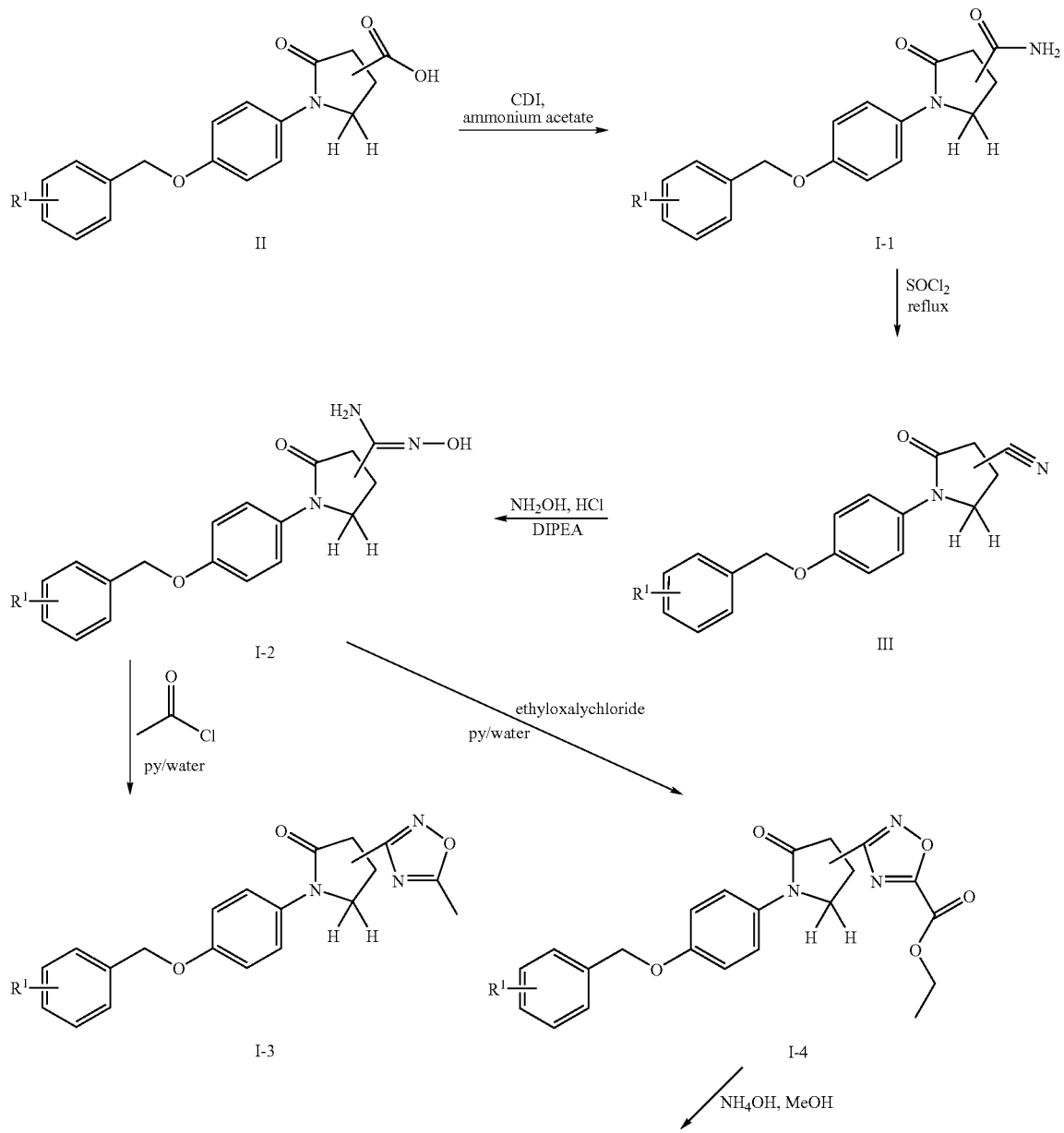

Scheme 1

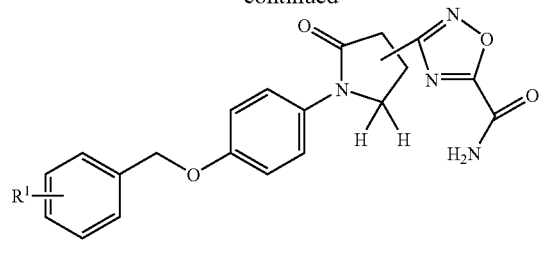

I-5

The definition of $R^1$ is as described above

Other compounds of general formula I can be manufactured by reacting a compound of formula II with thionyl chloride in the presence of catalytic N,N'-dimethylformamide to give the intermediate acid chloride which reacts with trimethylsilyldiazomethane and hydrobromic acid 33% in acetic acid to give the 2-bromo acetyl compound I-6. Compounds of formula I wherein $R^2$ signifies imidazole (I-8) can be prepared by refluxing compounds of formula I-6 with formamide and water. Compounds of formula I wherein $R^2$ signifies thiazol (I-7) can be prepared by refluxing compounds of formula I-6 with thioacetamide in a solvent like tetrahydrofuran.

Other compounds of formula I wherein $R^2$ signifies an amide, like methoxy methyl amide (I-9), can be prepared from the corresponding acid of formula II and 1,1'-carbonyldiimidazole (CDI) in N,N'-dimethylformamide (DMF) to give an activated intermediate that reacts with the corresponding amine like the methoxy methyl amine. The methoxy methyl amide I-9 reacts with nucleophiles like alkylmagnesium bromide, e.g. methyl magnesium bromide, to give the corresponding ketone of formula I-10.

Scheme 2

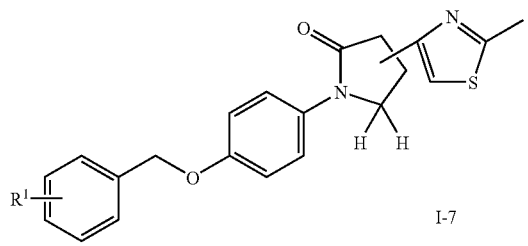

I-7

↑ thioacetamide THF

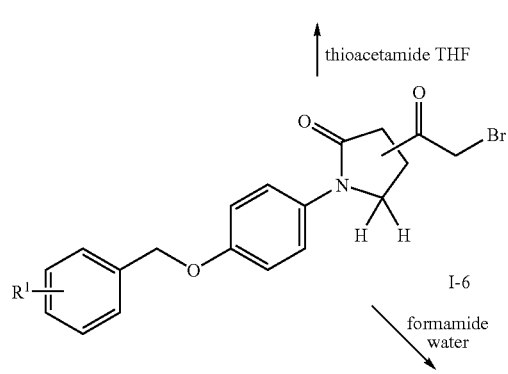

I-6

↘ formamide water

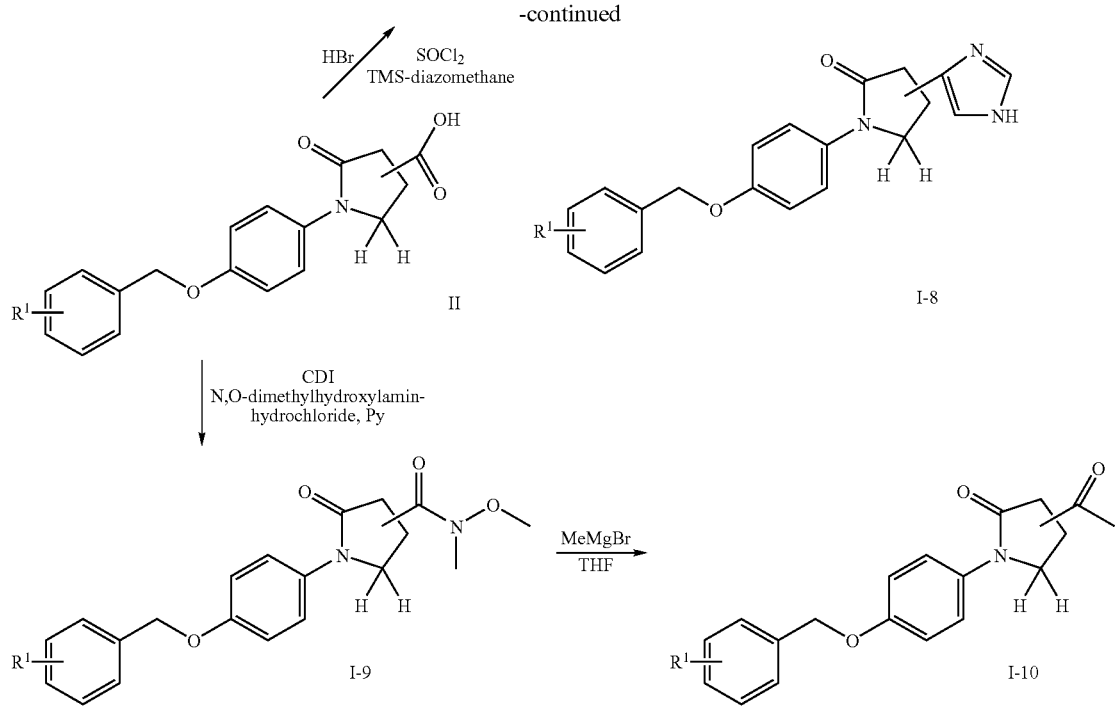

The substituent R¹ has the meaning as described above.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The pharmacological activity of the compounds was tested using the following method:

The cDNA's encoding human MAO-A and MAO-B were transiently transfected into EBNA cells using the procedure described by Schlaeger and Christensen [Cytotechnology 15:1-13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectro-photometric assay adapted from the method described by Zhou and Panchuk-Voloshina [Analytical Biochemistry 253:169-174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horse-radish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B.

IC$_{50}$ values were determined from inhibition curves obtained using nine inhibitor concentrations in duplicate, by fitting data to a four parameter logistic equation using a computer program.

The compounds of the present invention are specific MAO-B inhibitors. The IC$_{50}$ values of compounds of formula I as measured in the assay described above are in the range of 1 μM or less, and ideally 0.1 μM or less. The below table shows exemplary IC$_{50}$ values of compounds of formula I in one of their enantiomeric forms:

| Example | human MAO-B [IC$_{50}$ (μM)] |
|---|---|
| 3 | 0.018 |
| 4 | 0.016 |
| 5 | 0.043 |
| 6 | 0.429 |
| 8 | 0.387 |
| 9 | 0.187 |
| 10 | 0.392 |
| 11 | 0.011 |

The present invention also provides pharmaceutical compositions containing Pharmaceutical Compounds and in pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more Pharmaceutical Compound, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, e.g., as such carriers for tablets, coated tablets, dragées and hard gelatine capsules. Suitable carriers for soft gelatine capsules are, e.g., vegetable oils, waxes, fats, semi-solid and liquid polyols and the like; depending on the nature of the active substance no carriers are, however, usually required in the case of soft gelatine capsules. Suitable carriers for the production of solutions and syrups are, e.g., water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, e.g., natural or hardened oils, waxes, fats, semi-liquid or liquid polyols and the like.

In addition, the pharmaceutical compositions of the invention can contain preservatives, solubilizers, stabilizers, wetting agents, emulsifiers, sweeteners, colorants, flavorants, salts for varying the osmotic pressure, buffers, masking agents or antioxidants. They also can contain other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

Pharmaceutical Compounds are selective MAO-B antagonists. Therefore, the present invention also provides methods of treating diseases that are mediated by monoamine oxidase B. Such methods include administering a therapeutically effective amount of a Pharmaceutical Compound to an individual in need of such treatment. In one embodiment, the invention provides a method for treating Alzheimer's disease, which comprises administering to an individual a therapeutically effective amount of a compound of formula I. The invention also provides a method for treating senile dementia, which comprises administering to an individual a therapeutically effective amount of a compound of formula I. The invention further provides a method for treating cognitive impairment, which comprises administering to an individual a therapeutically effective amount of a compound of formula I.

Pharmaceutical Compounds and the compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. Pharmaceutical Compounds and compositions also can be administered rectally, for example, in the form of suppositories, or parenterally, for example, in the form of injectable solutions.

The dosage at which the compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided for illustration of the invention. They should not be considered as limiting the scope of the invention, but merely as being representative thereof.

EXAMPLE 1

(R)-1-[4-(3-Fluoro-benzyloxy)-phenyl]-5-oxo-pyrrolidine-3-carboxylic acid amide (R)-1-[4-(3-Fluoro-benzyloxy)-phenyl]-5-oxo-pyrrolidine-3-carboxylic acid (1.5 g, 0.005 mol) was dissolved in dry N,N-dimethylformamide under argon and cooled to 0° C. 1,1'-Carbonyl-diimidazole (1.4 g, 0.009 mol) was added to the mixture and the reaction stirred for one hour while the temperature rose from 0° C. to room temperature. Ammonium acetate (5.6 g, 0.073 mol) was added and the reaction was stirred for one hour at room temperature. Water was added dropwise to the mixture and a precipitate appeared. The solid was filtrated, washed with water and dried under vacuum to yield 1.36 g (0.0041 mol, 91% of theory) of the title compound as a white solid. MS (m/e)=329.3(M+H)$^+$.

EXAMPLE 2

(R)-1-[4-(3-Fluoro-benzyloxy)-phenyl]-5-oxo-pyrrolidine-3-carbonitrile

A mixture of (R)-1-[4-(3-fluoro-benzyloxy)-phenyl]-5-oxo-pyrrolidine-3-carboxylic acid amide (0.400 g, 0.001 mol) and thionyl chloride (2.3 ml, 0.032 mol) was refluxed under argon for 3 hours. The mixture was cooled to room temperature, diluted with 5 ml tetrahydrofuran, concentrated under vacuum and purified by column chromatography on silica gel using a 2:3-mixture of ethyl acetate and hexane as the eluent. The product fractions were concentrated to dryness to yield (0.106 g, 28% of theory) of a light brown oil. MS (m/e)=311.1 (M+H)$^+$.

EXAMPLE 3

(R)-1-[4-(3-Fluoro-benzyloxy)-phenyl]-N-hydroxy-5-oxo-pyrrolidine-3-carboxamidine (R)-1-[4-(3-Fluoro-benzyloxy)-phenyl]-5-oxo-pyrrolidine-3-carbonitrile (0.211 g, 0.001 mol) and hydroxylamine hydrochloride (0.047 g, 0.001 mol) were dissolved in ethanol (4 ml) and N,N-diisopropylethylamine (0.120 ml, 0.001 mol) was added. The reaction mixture was stirred under reflux for three hours. The reaction was cooled to room temperature, the solvent was evaporated and the residue extracted with dichloromethane and purified by column chromatography on silica gel using a 19:1-mixture of dichloromethane and methanol as the eluent to yield (0.220 g, 94% of theory) of a yellow oil. MS (m/e)=344.3(M+H)$^+$.

EXAMPLE 4

(R)-1-[4-(3-Fluoro-benzyloxy)-phenyl]-4-(5-methyl-[1,2,4]oxadiazol-3-yl)-pyrrolidin-2-one (R)-1-[4-(3-Fluoro-benzyloxy)-phenyl]-N-hydroxy-5-oxo-pyrrolidine-3-carboxamidine (0.020 g, 0.58 mmol) was dissolved in a mixture of 0.4 ml pyridine and acetyl chloride (0.01 ml, 0.116 mmol) was slowly added at 0° C. The mixture was then stirred at 70° C. overnight. Iced water was added and the mixture was stirred for one hour. Extraction with a saturated solution of ammonium chloride and dichloromethane gave the crude product that was purified by column cromatography on silica gel using a 19:1-mixture of dichloromethane and methanol as the eluent to obtain the title compound as a light yellow solid (0.0197 g, 92% of theory). MS (m/e)=368.4 (M+H)$^+$.

EXAMPLE 5

3-{(R)-1-[4-(3-Fluoro-benzyloxy)-phenyl]-5-oxo-pyrrolidin-3-yl}-[1,2,4]oxadiazole-5-carboxylic acid ethyl ester (R)-1-[4-(3-Fluoro-benzyloxy)-phenyl]-N-hydroxy-5-oxo-pyrrolidine-3-carboxamidine (0.020 g, 0.58 mmol) was dissolved in a mixture of 0.4 ml pyridine and ethyl oxalyl chloride (0.01 ml, 0.116 mmol) was slowly added at 0° C. The mixture was then stirred at 70° C. for half an hour. Iced water was added and the mixture was stirred for one hour. Extraction with a saturated solution of ammonium chloride and dichloromethane gave the crude product that was purified by column cromatography on silica gel using a 2:1-mixture of ethyl acetate and hexane as the eluent to obtain the title compound as a light yellow solid (0.019 g, 77% of theory). MS (m/e)=426.3 (M+H)$^+$.

EXAMPLE 6

3-{(R)-1-[4-(3-Fluoro-benzyloxy)-phenyl]-5-oxo-pyrrolidin-3-yl}-[1,2,4]oxadiazole-5-carboxylic acid amide 3-{(R)-1-[4-(3-Fluoro-benzyloxy)-phenyl]-5-oxo-pyrrolidin-3-yl}-[1,2,4]oxadiazole-5-carboxylic acid ethyl ester (0.110 g, 0.25 mmol) was dissolved in 3.5 ml of ammonia (2 M solution in methanol). The resulting mixture was stirred at 50° C. for half an hour. The mixture was cooled at 0° C. and a solid precipitated. The reaction mixture was filtrated and the solid washed with hexane and dried under vacuum. The residue was suspended in ethyl acetate and heated to reflux. Diethyl ether was added and the suspension cooled to 0° C. and filtrated to yield the title compound as a light brown solid (0.045 g, 44% of theory). MS (m/e)=397.4 (M+H)$^+$.

EXAMPLE 7

(R)-4-(2-Bromo-acetyl)-1-[4-(3-fluoro-benzyloxy)-phenyl]-pyrrolidin-2-one (R)-1-[4-(3-Fluoro-benzyloxy)-phenyl]-5-oxo-pyrrolidine-3-carboxylic acid (0.204 g, 0.62 mmol) was dissolved in a mixture of dichloromethane (4 ml), thionyl chloride (0.15 ml, 2.1 mmol) and a catalytic amount of N,N-dimethylformamide. The reaction mixture was stirred for half an hour at room temperature to form the intermediate acylchloride. Thereafter, the solvent was removed under reduced pressure and the residue suspended in toluene, concentrated under vacuum and dried. The resulting oil was dissolved in acetonitrile (2 ml) and trimethylsilyldiazomethane (2 M in hexane) (1.55 ml, 3.1 mmol) was added under argon. The resulting yellow solution was stirred at room temperature for half an hour until the diazoketone could be observed. After cooling of the the reaction mixture to 0° C., hydrobromic acid (33% in acetic acid) (0.71 ml, 4 mmol) was added dropwise. The resulting dark solution was stirred for half an hour at room temperature. Sodium bicarbonate (5 ml) was added and the mixture extracted with dichloromethane. The organic layers were dried over magnesium sulphate, filtrated and evaporated to dryness to give a residue that was purified by column cromatography on silica gel using a 1:1-mixture of ethyl acetate and hexane as the eluent to obtain the title compound as a light yellow oil (0.067 g, 67.5% yield of theory). MS (m/e)=407.3(M+H)$^+$.

EXAMPLE 8

(R)-1-[4-(3-Fluoro-benzyloxy)-phenyl]-4-(2-methyl-thiazol-4-yl)-pyrrolidin-2-one (R)-4-(2-Bromo-acetyl)-1-[4-(3-fluoro-benzyloxy)-phenyl]-pyrrolidin-2-one (0.040 g, 0.098 mmol) was dissolved in tetrahydrofuran (1 ml) and thioacetamide (0.007 g, 0.098 mmol) was added and the mixture was stirred at 40° C. for 24 hours. The tetrahydrofuran was evaporated and the residue was purified by column chromatography on silica gel using at first a 1:1-mixture then a 4:1-mixture of ethyl acetate and hexane as the eluent to yield the title compound as a light yellow solid (0.030 g, 80% of theory). MS (m/e)=383.3 (M+H)$^+$.

EXAMPLE 9

(R)-1-[4-(3-Fluoro-benzyloxy)-phenyl]-4-(1H-imidazol-4-yl)-pyrrolidin-2-one (R)-4-(2-Bromo-acetyl)-1-[4-(3-fluoro-benzyloxy)-phenyl]-pyrrolidin-2-one (0.050 g, 0.123 mmol) was dissolved in water (0.1 ml) and formamide (0.6 ml) was added and the mixture stirred at reflux for 6 hours. 2M HCl was added and the mixture extracted with ethyl acetate. The aqueous layer was neutralized with an aqueous solution (10%) of sodium hydroxide (pH 7-8) and extracted again with ethyl acetate to give a crude material which is subjected to chromatography on silica gel using a 19:1-mixture of dichloromethane and methanol as the eluent. There were obtained 0.011 g (25% of theory) of the title compound as a colorless solid. MS: m/e=352.4 (M+H)$^+$.

EXAMPLE 10

(R)-1-[4-(3-Fluoro-benzyloxy)-phenyl]-5-oxo-pyrrolidine-3-carboxylic acid methoxy-methyl-amide (R)-1-[4-(3-Fluoro-benzyloxy)-phenyl]-5-oxo-pyrrolidine-3-carboxylic acid (0.200 g, 0.001 mol) was dissolved in dry N,N-dimethylformamide (1 ml) under argon and the solution cooled to 0° C. 1,1'-Carbonyl-diimidazole (0.108 g, 0.001 mol) was added to the mixture and the reaction stirred for one hour while the temperature rose from 0° C. to room temperature. After the addition of N,O-dimethylhydroxylamine hydrochloride (0.063 g, 0.001 mol) and pyridine (0.053 ml, 0.001 mmol), the reaction was stirred for two hours at room temperature. Water (10 ml) and hydrochloric acid (0.1 N) was added and the mixture extracted with ethyl acetate. The organic phase was washed with a solution of sodium carbonate (1 M) and extracted again with ethyl acetate to yield 0.225 g (99% of theory). The crude product obtained in this way was used in the next step without further purification. MS: m/e=373.4(M+H)$^+$.

EXAMPLE 11

(R)-4-Acetyl-1-[4-(3-fluoro-benzyloxy)-phenyl]-pyrrolidin-2-one (R)-1-[4-(3-Fluoro-benzyloxy)-phenyl]-5-oxo-pyrrolidine-3-carboxylic acid methoxy-methyl-amide (0.050 g, 0.143 mmol) was dissolved under argon in tetrahydrofurane (1 ml) and methyl magnesium bromide (0.188 mmol, 0.063 ml) was added at 0° C. The resulting solution was stirred at 0° C. for two hours. Water was added at 0° C. and the mixture was stirred for one hour. Extraction with ethyl acetate gave a residue which after chromatography on silica gel using a 9:1-mixture of ethyl acetate and cyclohexane as the eluent yielded 0.040 g (91% of theory) of the title compound as a white solid. MS: m/e=328.4 (M+H)$^+$.

EXAMPLE A

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone 1 | 2 |
| Na carboxymethylstarch | 20 |
| Magnesium stearate | 4 |
| Tablet weight | 400 |

EXAMPLE C

Capsules of the following composition are produced:

| | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution can have the following composition and is manufactured in usual manner:

| | |
|---|---|
| Active substance | 1.0 mg |
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

The invention claimed is:
1. A compound of formula I

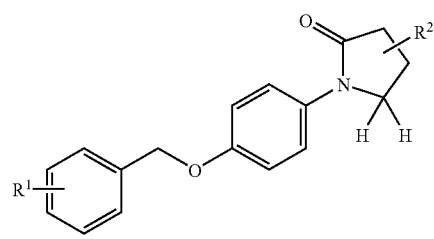

wherein
R$^1$ is halogen;
R$^2$ is —C(NH$_2$)=N—OH, —C(O)CH$_2$Br, —C(O)N(CH$_3$)OCH$_3$ or —C(O)-lower alkyl, or is a 5-membered heteroaryl group containing 2 or 3 heteroatoms selected from the group consisting of N, O and S, optionally substituted by R³, wherein R³ is lower alkyl, —NR'R" or —C(O)R;

R is NR'R", lower alkyl, or lower alkoxy; and

R' and R" are each independently hydrogen or lower alkyl; or a pharmaceutically acceptable salt thereof.

2. A compound according to claim 1 having formula IA,

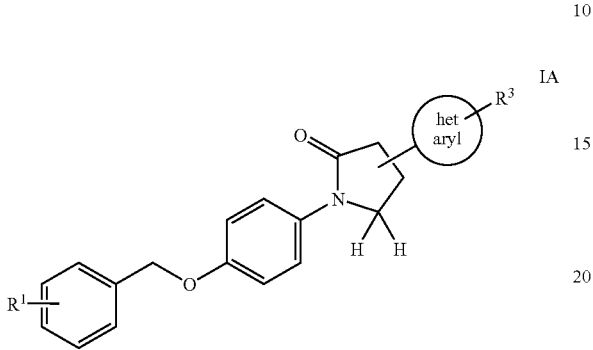

wherein hetaryl is a 5-membered heteroaryl group containing 2 or 3 heteroatoms selected from the group consisting of N, O and S.

3. A compound of formula IA according to claim 2, selected from the group consisting of
- (R)-1-[4-(3-fluoro-benzyloxy)-phenyl]-4-(5-methyl-[1,2,4]oxadiazol-3-yl)-pyrrolidin-2-one,
- 3-{(R)-1-[4-(3-fluoro-benzyloxy)-phenyl]-5-oxo-pyrrolidin-3-yl}-[1,2,4]oxadiazole-5-carboxylic acid ethyl ester,
- 3-{(R)-1-[4-(3-fluoro-benzyloxy)-phenyl]-5-oxo-pyrrolidin-3-yl}-[1,2,4]oxadiazole-5-carboxylic acid amide,
- (R)-1-[4-(3-fluoro-benzyloxy)-phenyl]-4-(2-methyl-thiazol-4-yl)-pyrrolidin-2-one, and
- (R)-1-[4-(3-fluoro-benzyloxy)-phenyl]-4-(1H-imidazol-4-yl)-pyrrolidin-2-one.

4. A compound of formula I according to claim 1, wherein the 5-membered heteroaryl group containing 2 or 3 heteroatoms is [1.2.4]oxadiazolyl, optionally substituted by R³.

5. A compound of formula I according to claim 1, wherein the 5-membered heteroaryl group containing 2 or 3 heteroatoms is 1,3-thiazolyl, optionally substituted by R³.

6. A compound of formula I according to claim 1, wherein the 5-membered heteroaryl group containing 2 or 3 heteroatoms is imidazolyl, optionally substituted by R³.

7. A compound of formula I according to claim 1, wherein R² is —C(NH₂)=N—OH, —C(O)CH₂Br, —C(O)N(CH₃)OCH₃ or —C(O)-lower alkyl.

8. A compound of formula I according to claim 7, selected from the group consisting of
- (R)-1-[4-(3-fluoro-benzyloxy)-phenyl]-N-hydroxy-5-oxo-pyrrolidine-3-carboxamidine,
- (R)-1-[4-(3-fluoro-benzyloxy)-phenyl]-5-oxo-pyrrolidine-3-carboxylic acid methoxy-methyl-amide, and
- (R)-4-acetyl-1-[4-(3-fluoro-benzyloxy)-phenyl]-pyrrolidin-2-one.

9. A compound of formula I according to claim 7, wherein R² is —C(NH₂)=N—OH.

10. A compound of formula I according to claim 7, wherein R² is —C(O)CH₂Br.

11. A compound of formula I according to claim 7, wherein R² is —C(O)N(CH₃)OCH₃.

12. A compound of formula I according to claim 7, wherein R² is —C(O)-lower alkyl.

13. A pharmaceutical composition comprising a therapeutically effective amount of a compound of formula I

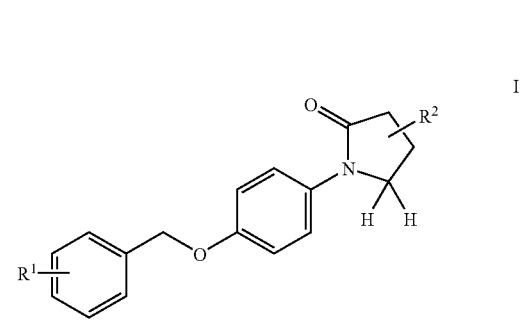

wherein
R¹ is halogen;
R² is —C(NH₂)=N—OH, —C(O)CH₂Br, —C(O)N(CH₃)OCH₃, CN or —C(O)-lower alkyl, or is a 5-membered heteroaryl group containing 2 or 3 heteroatoms selected from the group consisting of N, O and S, optionally substituted by R³, wherein R³ is lower alkyl, —NR'R" or —C(O)R;
R is NR'R", lower alkyl, or lower alkoxy, and
R' and R" are each independently hydrogen or lower alkyl;
or a pharmaceutically acceptable salt thereof and a pharmaceutically acceptable carrier.

14. A composition according to claim 13, wherein the compound of formula I is a compound of formula IA

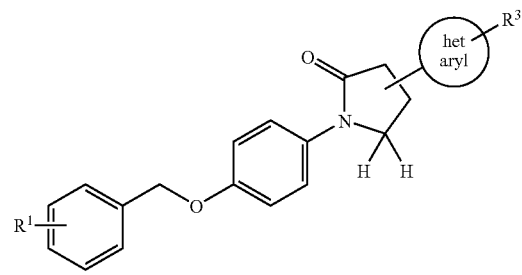

wherein hetaryl is a 5-membered heteroaryl group containing 2 or 3 heteroatoms selected from the group consisting of N, O and S.

15. A method for treating Alzheimer's disease or senile dementia comprising administering to an individual a therapeutically effective amount of a compound of formula I

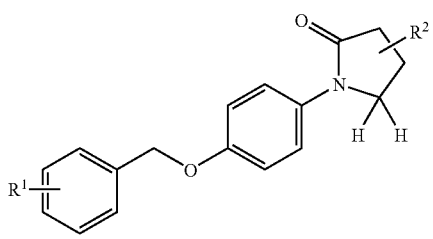

wherein
R¹ is halogen;
R² is —C(NH₂)=N—OH, —C(O)CH₂Br, —C(O)N(CH₃)OCH₃, or —C(O)-lower alkyl, or is a 5-membered heteroaryl group containing 2 or 3 heteroatoms selected from the group consisting of N, O and S, optionally substituted by R³, wherein R³ is lower alkyl, —NR'R" or —C(O)R;
R is NR'R", lower alkyl, or lower alkoxy; and
R' and R" are each independently hydrogen or lower alkyl;
or a pharmaceutically acceptable salt thereof.

16. The method of claim 15, wherein the compound of formula I is a compound of formula IA

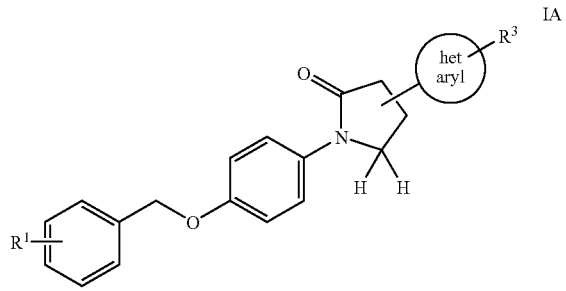

wherein hetaryl is a 5-membered heteroaryl group containing 2 or 3 heteroatoms selected from the group consisting of N, O and S.

* * * * *